United States Patent [19]
Beutner et al.

[11] Patent Number: 5,498,418
[45] Date of Patent: Mar. 12, 1996

[54] NITROGLYCERINE PLASTER AND PROCESS FOR ITS PRODUCTION

[75] Inventors: Dieter Beutner, Monheim; Henning von Knobelsdorff, Bonn; Hans-Michael Wolff, Monheim; Rainer Hoffmann, Neuwied; Reinhold Meconi, Neuwied; Robert P. Klein, Neuwied, all of Germany

[73] Assignees: Schwarz Pharma AG, Monheim; LTS Lohmann Therapie-Systemme GmbH & Co. KG, Neuwied, both of Germany

[21] Appl. No.: 142,316
[22] PCT Filed: May 25, 1992
[86] PCT No.: PCT/EP92/01169
§ 371 Date: Mar. 14, 1994
§ 102(e) Date: Mar. 14, 1994
[87] PCT Pub. No.: WO92/22292
PCT Pub. Date: Dec. 23, 1992

[30] Foreign Application Priority Data

Jun. 10, 1991 [DE] Germany .......... 41 18 891.8

[51] Int. Cl.$^6$ .......... A61F 13/00
[52] U.S. Cl. .......... 424/448; 424/449
[58] Field of Search .......... 424/448, 449

[56] References Cited

U.S. PATENT DOCUMENTS 4,994,267  2/1991  Sablotsky .......... 514/182

FOREIGN PATENT DOCUMENTS

| | | |
|---|---|---|
| 0062682 | 10/1982 | European Pat. Off. . |
| 0272562 | 6/1988 | European Pat. Off. . |
| 0285550 | 10/1988 | European Pat. Off. . |
| 0427877 | 5/1991 | European Pat. Off. . |
| 0435199 | 7/1991 | European Pat. Off. . |
| 0450986 | 10/1991 | European Pat. Off. . |
| 62-292877 | 12/1987 | Japan . |
| 2086224 | 5/1982 | United Kingdom . |
| 8606281 | 11/1986 | WIPO . |

OTHER PUBLICATIONS

Chemical Abstracts, vol. 97, No. 12, Sep. 1982, Abstract No. 98386f.

*Primary Examiner*—D. Gabrielle Phelan
*Attorney, Agent, or Firm*—Meltzer, Lippe, Goldstein et al.

[57] ABSTRACT

The invention relates to a dermal plaster for the transdermal provision of nitroglycerin comprising a carrier film and a removable protective film and an adhesive mass containing nitroglycerine on the basis of a cross-linked acrylate-vinyl acetate copolymer in which the monomer mix used for polymerization consists essentially of 21 to 40% wt. vinyl acetate, 55 to 70% wt. of an acrylic acid C2–8 alkyl ester and 3 to 10% wt. of an acrylic acid C2–4 hydroxyalkyl ester and which is cross-linked by heating and the removal of any solvents present after the addition of a cross-linking agent and the nitroglycerin.

6 Claims, 2 Drawing Sheets

NITROGLYCERINE PLASTER AND PROCESS FOR ITS PRODUCTION

This application is a 371 of PCT/EP92/01169 filed May 25, 1992. The invention relates to a dermal plaster for the transdermal administration of nitroglycerine, comprising a carrier film and a nitrogylcerine-containing adhesive body on the basis of a crosslinked acrylate copolymer. The plaster also has a protective film which is removed by pulling off prior to the use of the plaster—i.e., prior to its application to the skin.

Many dermal plasters for the transdermal administration of nitroglycerine are known. For example, DE 2135533 and DE 3315272 disclose plasters which are built up from a number of layers and control the delivery of the active agent. Nitroglycerine is released by different mechanisms, either from a single-layer reservoir via a control membrane (DE 2135533), or by a particular design of the multi-layer reservoir (DE 3315272). Since multilayer dermal plasters are very expensive, more particularly to manufacture, in the recent past plasters have been developed which consist of a single layer in addition to the carrier film. In order to enable sufficient nitroglycerine to be absorbed and again adequately delivered to the skin, various self-adhesive adhesive substances have been developed with the most various properties as regards absorptivity of active agent, delivery of active agent and adhesive properties to the skin. As examples, the following may be mentioned: GB A 2095108, DE OS 3231400, GB A 2086224, EP A 0062682, EP 85903926.5, EP 86902978.5, EP 0285550, EP 0272562, US 4608249 and DE PS 3200369. In dependence on the materials used and the degree of crosslinkage, the plasters have different absorptive capacity and delivery capacity for nitroglycerine and are characterized by varying adhesive capacity to the skin. Varying skin compatibility also plays a considerable role. Many plasters also contain substances for increasing the transepidermal transport of substances (so-called resorption accelerators).

It is an object of the invention to provide a dermal plaster for the transdermal administration of nitroglycerine which is characterized by the use of an adhesive which has not only as high an absorptive capacity as possible, but also a high delivery capacity for nitroglycerine, so that the release surface of the plaster can be small with the necessary quantity released per day, and therefore the cost of the plaster is as low as possible. At the same time, the use of a special adhesive simplifies the production process, makes it inexpensive and economizes on the addition of resorption accelerators. This simplification of the pharmaceutical formulation at the same time reduces the risk of skin irritations and/or of any uncontrollable change in the nitroglycerine concentration in the adhesive body, something which may accompany the penetration of resorption accelerators from the adhesive into the skin.

The dermal plaster according to the invention for the transdermal administration of nitroglycerine, comprising a carrier foil, a nitroglycerine-containing adhesive on the basis of a crosslinked acrylate-vinyl acetate copolymer, and a conventional removable protective film is characterized in that the nitroglycerine-containing adhesive substance is obtained by the radical polymerization in a first stage of a mixture consisting of 21 to 40% by weight vinyl acetate, 55 to 70% by weight of an acrylic acid-$C_{2-8}$-alkyl ester and 3 to 10% by weight of an acrylic acid-$C_{2-4}$-hydroxyl acryl ester, with 100% by weight monomers in the mixture, in an organic solvent, whereafter in a second stage a conventional crosslinkage agent in an organic solvent and the nitroglycerine in the quantity required for the intended use of the plaster is admixed, if necessary in an organic solvent, and finally in a third stage the resulting mixture or the particular acrylate-vinyl acetate copolymer is crosslinked in an additional stage, accompanied by heating and the removal of the organic solvent or mixture of solvents used, and the resulting nitroglycerine is "built into" the adhesive substance in a special manner by the subsequent and additional crosslinkage of the special acrylate-vinyl acetate copolymer. The acrylate-vinyl acetate copolymer has a relative viscosity of 3.0 to 4.2.

Preferably the mixture of monomers contains 2-ethylhexyl acrylate and hydroxyethyl acrylate in addition to vinyl acetate. Preferably the subsequent crosslinkage of the special acrylate-vinyl acetate copolymer is performed with a titanium acid ester consisting of polybutyl titanate and/or titanium acetyl acetonate, more particularly in a quantity of 0.3 to 3% by weight thereof, the percentages by weight being related to the weight of the copolymer.

The process for the production of the plaster according to the invention is characterized in that a solution of a copolymer, containing nitroglycerine in the quantity required for the intended use of the plaster and a conventional crosslinkage agent or a conventional mixture of crosslinkage agents and obtained by the radical polymerization of a mixture of monomers consisting of 21 to 40% by weight vinyl acetate, 55 to 70% by weight of an acrylic acid-$C_{2-8}$-alkyl ester and 3 to 10% by weight of an acrylic acid-$C_{2-4}$-hydroxyl alkyl ester, is applied in the required layer thickness to the protective film of the plaster, and the solvent or mixture of solvents is removed accompanied by heating, the additional crosslinkage of the special acrylate-vinyl acetate copolymer being thereby performed.

Preferably the process is characterized in that the acrylate-vinyl acetate copolymer, nitroglycerine and crosslinkage agent are dissolved in a solvent which contains 20 to 40% by weight ethanol or an ethanol-methanol mixture, with a solids proportion consisting of 40 to 60% by weight of the mixture of the special acrylate-vinyl acetate copolymer, crosslinkage agent and nitroglycerine.

Embodiment

Process for the production of dermal plasters for the transdermal administration of nitroglycerine according to the present invention, quantities stated being related to a starting mixture of 100 m$^2$.

4.00 kg nitroglycerine in oil form were slowly added to 16.00 kg of a 40% solution (w/w) of the acrylate-vinyl acetate copolymer, accompanied by intensive mixing. Then the mixture was homogenized by agitation. The result was a 20% (w/w) solution of nitroglycerine in this adhesive solution.

The acrylate-vinyl acetate copolymer was prepared as follows:

Of the total quantity of 112 g vinyl acetate, 270 g 2-ethylhexyl acrylate, 20 g hydroxyethyl acrylate, 1.4 g azodiisobutyronitrile and 407 g ethyl acetate, 112 g vinyl acetate, 39 g 2-ethylhexyl acrylate, 3 g hydroxyethyl acrylate and 0.5 g azodiisobutyronitrile were added to 115 g ethyl acetate and heated to reflux. The residual proportion of components was added over a period of 4 hours with constant reflux. After the completion of polymerization the mixture was cooled to room temperature. The resulting adhesive polymer solution had a viscosity of 5300 mPa.s at 25° C., measured with a Brookfield viscometer, a solids proportion of 47.9% and a relative viscosity of 3.1.

To this solution 1.35 titanium acetyl acetonate and sufficient ethanol or ethanol-ethyl acetate mixture was added to adjust the solids content in the product to 40%.

EXAMPLE 1

Figure 1:
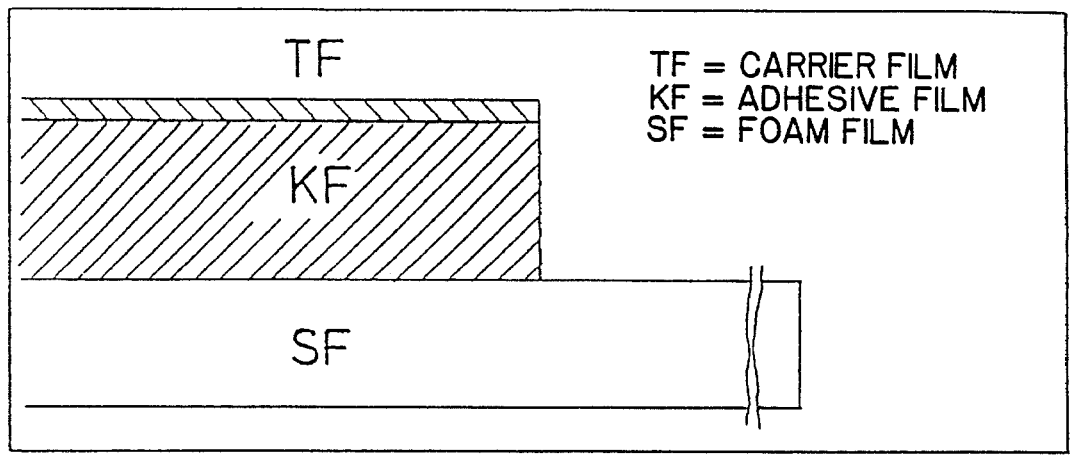
FIG. 1 illustrates a cross-section of a plaster in accordance with the present invention.
Figure 2:
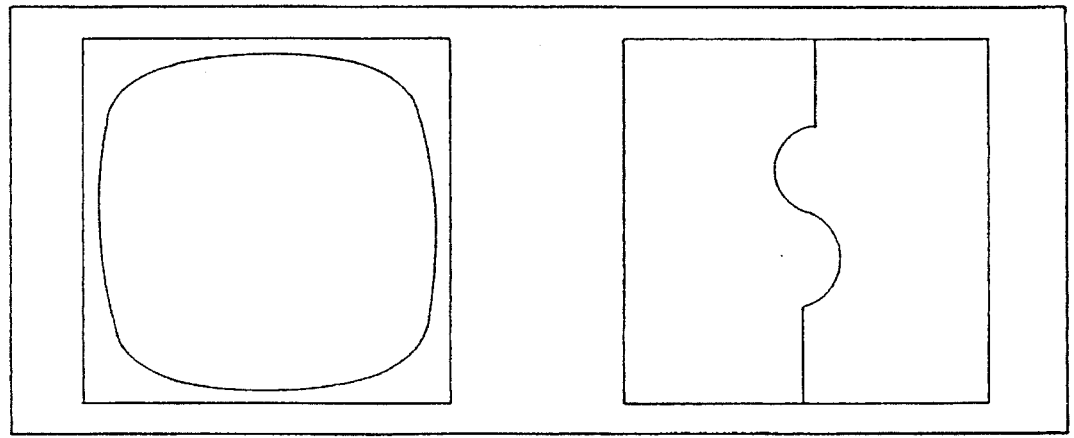
FIG. 2 shows front and rear views of a punched plaster in accordance with the present invention.

The aforementioned adhesive solution, containing 20% (w/w) nitroglycerine was applied to a siliconized polyester film 100 μm thick, so that after the removal of the solvent a film having a weight per unit area of 92 g/m$^2$ was the result. The film was covered with a 19 μm thick polyester film and punched to form plasters having a contact area of 16 cm$^2$ (FIGS. 1 and 2). A dermal plaster thus produced having a weight of 420 mg contained 55 mg nitroglycerine.

To assess the release behaviour of the active agent in vitro, a plaster having a punched-out surface of 3.14 cm$^2$ was attached in a modified Franz diffusion cell (cf. Chien, Yie W., Drugs of Today Vol. 23, No. 11 (1987) 625–646) to a skin preparation of hairless mice.

Figure 3:
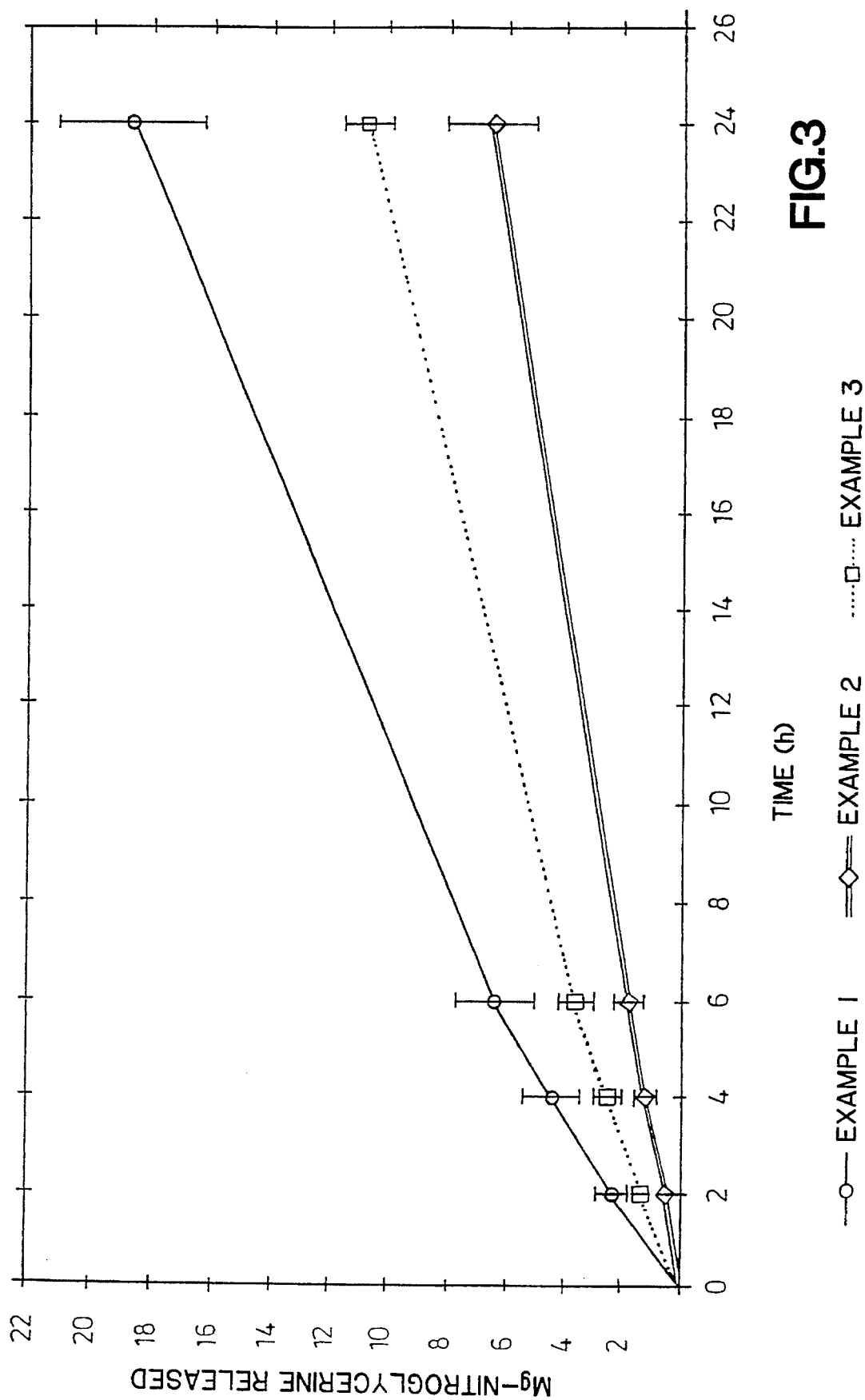
FIG. 3 shows a nitroglycerine release profile from a dermal plaster in accordance with the present invention.

Then the cell was immediately filled air-bubble-free with 18.00 ml isotonic phosphate buffer solution (32±0.5° C.) and thermostated to 32±0.5° C. After 2, 4, 6 and 24 hours the release medium was replaced by fresh solution thermostated to 32±0.5° C. The solution removed was investigated for its nitroglycerine content by HPLC chromatography (Lit.: Pharm. Biol. 4, 32 (1981)). FIG. 3 shows the release profile measured by this method for a plaster 16 cm$^2$ in size.

The average nitroglycerine release rates (±S.D.) were (n=3):

after 2 hours 2.32±0.56 mg/16 cm$^2$ after 4 hours 4.42±1.00 mg/16 cm$^2$ after 6 hours 6.43±1.33 mg/16 cm$^2$ after 24 hours 18.74±2.43 mg/16 cm$^2$

EXAMPLE 2

0.8% (w/w) titanium acetyl acetonate (Manufacturers: Dynamit Nobel Nederland B.V., 75% (w/w) solution in isopropanol), related to a 40% (w/w) solids proportion of the polyacrylate solution plus nitroglycerine, was additionally added to the aforementioned adhesive solution containing 20% (w/w) nitroglycerine and the mixture was homogenized. The solution was applied to a siliconized polyester film having a thickness of 100 μm, so that after the removal of the solvent, a film having a surface weight of 93 g/m$^2$ was the result. The film was covered with a 19 μm thick polyester film and punched to give plasters having a contact area of 16 cm$^2$ (FIGS. 1 and 2). A dermal plaster thus produced having a weight of 420 mg contained 55 mg nitroglycerine.

The release of active substance in vitro was performed in accordance with the method of Example 1. FIG. 3 also shows in graph form the corresponding release profile.

The average nitroglycerine release rates (±S.D.) were (n=3):

after 2 hours 0.54±0.20 mg/16 cm$^2$ after 4 hours 1.20±0.37 mg/16 cm$^2$ after 6 hours 1.78±0.53 mg/16 cm$^2$ after 24 hours 6.60±1.56 mg/16 cm$^2$

EXAMPLE 3

The aforementioned adhesive solution, containing 20% (w/w) nitroglycerine was applied to a siliconized polyester film having a thickness of 100 μm, so that after the removal of the solvent a film having a weight per unit area of 64 g/m$^2$ was the result. The film was covered with a 19 μm thick polyester film and punched to give plasters having a contact area of 16 cm$^2$ (FIGS. 1 and 2). A dermal plaster thus produced having a weight of 360 mg contained 40 mg nitroglycerine. The release of active substance in vitro was performed in accordance with the method of Example 1. FIG. 3 also shows in graph form the corresponding release profile.

The average nitroglycerine release rates (±S.D.) were (n=3):

after 2 hours 1.27±0.29 mg/16 cm$^2$ after 4 hours 2.48±0.48 mg/16 cm$^2$ after 6 hours 3.56±0.60 mg/16 cm$^2$ after 24 hours 10.79±0.82 mg/16 cm$^2$.

We claim:

1. A dermal plaster for the transdermal administration of nitroglycerine, comprising a carrier film, a nitroglycerine-containing adhesive body formed from an acrylate-vinyl acetate copolymer, and a removable protective film, said adhesive body, being produced by:

1) subjecting a mixture of monomers consisting essentially of 21 to 40% by weight vinyl acetate, 55 to 70% by weight 2-ethylhexyl acrylate, and 3 to 10% by weight hydroxyethyl acrylate in an organic solvent to radical polymerization, said weight percentages being based on 100% by weight of said monomers.

2) admixing into said mixture of monomers a crosslinking agent and said nitroglycerine and 3) causing said monomers to crosslink while heating and removing said solvent.

2. The dermal plaster of claim 1, wherein said crosslinking agent is a titanium acid ester or a mixture of titanium acid esters.

3. The dermal plaster of claim 2, wherein said crosslinking agent comprises 0.3 to 3% by weight of a titanium acid ester or a mixture of titanium acid esters, said percentage by weight being based on the weight of said copolymer containing said crosslinking agent and obtained by radical polymerization.

4. The dermal plaster of claim 2, wherein said crosslinking agent is titanium acetyl acetonate, polybutyl titanate, or mixtures thereof.

5. A process for the production of a dermal plaster for the transdermal administration of nitroglycerine comprising forming a solution of an acrylate-vinyl acetate copolymer in an organic solvent, said acrylate-vinyl acetate copolymer consisting essentially of said nitroglycerine, a crosslinking agent, and a mixture of monomers which has been subjected to radical polymerization, said mixture of monomers including 21 to 40% by weight vinyl acetate, 55 to 70% by weight of 2-ethylhexyl acrylate, and 3 to 10% by weight of hydroxyethyl acrylate, said percentages by weight being based on the weight of said monomer mixture, applying said solution as a layer onto a protective film, removing the solvent in said solution while heating, said acrylate-vinyl acetate copolymer being thereby crosslinked, applying a carrier film on top of said layer containing said crosslinked acrylate-vinyl acetate copolymer, and cutting said plaster into a required size.

6. The process of claim 5, wherein said acrylate-vinyl acetate copolymer, said nitroglycerine, and said crosslinking agent are dissolved together in a solvent containing 20 to 40% by weight ethanol or an ethanol-methanol mixture, wherein said acrylate-vinyl acetate copolymer, said crosslinking agent, and said nitroglycerine comprise 40 to 60% by weight of said resulting mixture.

* * * * *